US012661361B2

(12) United States Patent
Taub

(10) Patent No.: US 12,661,361 B2
(45) **Date of Patent: *Jun. 23, 2026**

(54) RESMETIROM FOR REDUCING LIVER VOLUME

(71) Applicant: Madrigal Pharmaceuticals, Inc., West Conshohocken, PA (US)

(72) Inventor: Rebecca Taub, Villanova, PA (US)

(73) Assignee: Madrigal Pharmaceuticals, Inc., West Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/386,839

(22) Filed: Nov. 12, 2025

(65) Prior Publication Data

US 2026/0069598 A1 Mar. 12, 2026

Related U.S. Application Data

(63) Continuation of application No. 18/695,572, filed as application No. PCT/US2022/044826 on Sep. 27, 2022.

(60) Provisional application No. 63/248,634, filed on Sep. 27, 2021.

(51) Int. Cl.
*A61K 31/53* (2006.01)
*A61P 1/16* (2006.01)

(52) U.S. Cl.
CPC ................ *A61K 31/53* (2013.01); *A61P 1/16* (2018.01)

(58) Field of Classification Search
None
See application file for complete search history.

(56) References Cited

U.S. PATENT DOCUMENTS

| | | | |
|---|---|---|---|
| 7,452,882 | B2 | 11/2008 | Haynes et al. |
| 8,076,334 | B2 | 12/2011 | Haynes et al. |
| 11,090,308 | B2 | 8/2021 | Taub |
| 11,986,481 | B2 | 5/2024 | Kelly et al. |
| 12,102,646 | B2 | 10/2024 | Lian et al. |
| 2021/0122740 | A1 | 4/2021 | Mirmehrabi et al. |
| 2024/0051925 | A1 | 2/2024 | Confalone et al. |

FOREIGN PATENT DOCUMENTS

WO WO 2020/049556 * 3/2020 .......... A61K 31/575

OTHER PUBLICATIONS

Harrison et al (Treatment of cirrhotics with resmetirom in Phase 3 Maestro-NAFLD-1 NASH study open label arm effects on biomarkers and imagine, EASL Congress® 2021: Jun. 23-26, 2021) (Year: 2021).*

Harrison et al (Hepatology Comm 5:573-588, Apr. 2021) (Year: 2021).*

Madrigal Pharmaceuticals, Inc. "Press Release: Madrigal Pharmaceuticals Exceeds Target Enrollment in Phase 3 Maestro NAFLD-1 Trial" (Sep. 3, 2020) (Year: 2020).*

Tanaka et al (Pharmacol Ther 179:142-157, 2017) (Year: 2017).*

Kling ("NASH drug passes phase 2 trial", available online at https://www.mdedge.com/endocrinology/article/184420/hepatology/nash-drug-passes-phase-2-trial, Nov. 13, 2018) (Year: 2018).*

Bashir et al (Liver volume reduction in resmetirom-treated non-cirrhotic and cirrhotic NASH patients, AASLD Nov. 2021) (Year: 2021).*

International Search Report and Written Opinion mailed Dec. 22, 2022, directed to International Application No. PCT/US2022/044826; 13 pages.

Aimo Kannt et al., "Activation of thyroid hormone receptor-[beta] improved disease activity and metabolism independent of body weight in a mouse model of non-alcoholic steatohepatitis and fibrosis", British Journal of Pharmacology, Wiley-Blackwell, UK, vol. 178, No. 12, (Apr. 6, 2021) pp. 2412-2423, XP071089350, ISSN: 0007-1188, DOI: 10.1111/BPH.15427.

Harrison Stephen A et al.,"Resmetirom (MGL-3196) for the treatment of non-alcoholic steatohepatitis: a multicentre, randomised, double-blind, placebo-controlled, phase 2 trial", Lancet, Nov. 30, 2019, 394(10213):2012-2014, Published Online Nov. 11, 2019 https://doi.org/10.1016/S0140-6736(19)32517-6.

Feigh Michael et al., "NHS Core Content (Athens): Metabolic, biochemical, histopathological, and transcriptomic effects of resmetirom (MGL-3196) in the GAN diet-induced obese and biopsy confirmed mouse model of NASH", (Sep. 17, 2021), XP093007262, Retrieved from the Internet: URL:https://easl.eu/wpcontent/uploads/2021/09/02_NAFLD-2021-Abstract-book-FULL-web.pdf.

Anonymous, "NCT05500222: A Study to Evaluate the Effect of Resmetirom on Clinical Outcomes in Patients With Well-compensated NASH Cirrhosis", (Sep. 1, 2022), Internet, URL: https://clinicaltrials.gov/ct2/history/NCT05500222V_3=View#StudyPageTop , (Dec. 12, 2022), XP093007265 [IP].

Bashir Mustafa et al., "Liver Volume Reduction in Resmetirom Treated Non-Cirrhotic and Cirrhotic NASH Patients", (Nov. 1, 2021), URL: https://www.natap.org/2022/HCV/060322_05.htm, (Dec. 12, 2022), XP093007394 [XP].

Madrigal Pharmaceuticals, Inc., "Press Release: Madrigal Pharmaceuticals Exceeds Target Enrollment in Phase 3 Maestro NAFLD-1 Trial," Retrieved from: https://ir.madrigalpharma.com/node/13456/pdf, Sep. 3, 2020; 3 pages.

Madrigal Pharmaceuticals, Inc., "Press Release: Madrigal Pharmaceuticals Highlights Presentations at the Liver Meeting Digital ExperienceTM, The American Association for the Study of Liver Diseases Meeting Nov. 13, 2020, Including NASH Expert Insights on the Ongoing Open Label Arm of Resmetirom 52-W," Retrieved from: https://ir.madrigalpharma.com/node/13511/pdf, Nov. 13, 2020; 4 pages.

(Continued)

*Primary Examiner* — Craig D Ricci
(74) *Attorney, Agent, or Firm* — Venable LLP

(57) ABSTRACT

The present disclosure describes a method of reducing liver volume in a cirrhotic or non-cirrhotic subject, the method comprising administering resmetirom, a prodrug thereof, or a pharmaceutically acceptable salt of the resmetirom or the resmetirom prodrug. The present disclosure also describes a method of treating NASH in a cirrhotic subject in need thereof, the method comprising administering to the subject resmetirom, a prodrug thereof, or a pharmaceutically acceptable salt of the resmetirom or the resmetirom prodrug.

10 Claims, 6 Drawing Sheets

(56) References Cited

OTHER PUBLICATIONS

Madrigal Pharmaceuticals, Inc., "Press Release: Madrigal Pharmaceuticals Announces Presentation of Positive Clinical Data of Resmetirom from Open-Label Portion of Ongoing Phase 3 Clinical Trial Maestro-NAFLD-1 at the International Liver CongressTM 2021," Retrieved from: https://ir.madrigalpharma.com/node/13716/pdf, Jun. 25, 2021; 4 pages.
Madrigal Pharmaceuticals, Inc., "Press Release: Madrigal Pharmaceuticals Reports 2021 Second Quarter Financial Results and Provides Corporate Update," Retrieved from: https://ir.madrigalpharma.com/node/13756/pdf, Aug. 5, 2021; 5 pages.
Prescribing information: Rezdiffra (resmetirom) tablets, for oral use, revised Mar. 2024.
Harrison et al, "Treatment of cirrhotics with resmetirom in Phase 3 Maestro-NAFLD-1 Nash study open label arm: effects on biomarkers and imaging," Presented at EASL Congress™ 2021; Jun. 23-26, 2021; held online.
ClinicalTrials.gov Identifier NCT02912260, "Phase 2 Study of MGL-3196 in Patients With Non-Alcoholic Steatohepatitis (NASH)," Last Update Posted Dec. 19, 2017, 9 pages.
Kelly M. J., et al., "Discovery of 2-[3,5-Dichloro-4-(5-isopropyl-6-oxo-1,6-dihydropyridazin-3-yloxy)phenyl]-3,5 dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia," Journal of Medicinal Chemistry, 2014, 57, 10, 3912-3923.
Harrison et al., "MGL-3196, a selective thyroid hormone receptor-beta agonist significantly decreases hepatic fat in NASH patients at 12 weeks, the primary endpoint in a 36 week serial liver biopsy study," Journal of Hepatology, vol. 68, S38 (2018).
Harrison et al., "MGL-3196, a selective thyroid hormone receptor-beta agonist significantly decreases hepatic fat in NASH patients at 12 weeks, the primary endpoint in a 36 week serial liver biopsy study," The International Liver Congress, European Association for the Study of the Liver, Apr. 11-15, 2018.
Harrison et al., "Effects of Resmetirom on Noninvasive Endpoints in a 36-Week Phase 2 Active Treatment Extension Study in Patients With NASH," Hepatology Communications, vol. 5, pp. 573-588 (2021).
Harrison et al., "Reduction in Fibrosis and Steatohepatitis Imaging and Biomarkers in 52-Week Resmetirom Non-Alcoholic Steatohepatitis Trial," NAFLD Summit Poster, Sep. 16-17, 2021.
Ratziu et al., "Phase 3 development of resmetirom, a liver-directed thyroid hormone receptor (THR)-β agonist for the treatment of patients with NASH and significant liver fibrosis," Presented at ILC 2021 Madrigal Hosted Symposium, Jun. 25, 2021.

* cited by examiner

RESMETIROM FOR REDUCING LIVER VOLUME

CROSS REFERENCE TO RELATED APPLICATIONS

This application is a continuation of U.S. application Ser. No. 18/695,572, filed Mar. 26, 2024, which is a national stage entry under 35 U.S.C. § 371 of International Application No. PCT/US2022/044826, filed Sep. 27, 2022, which claims priority to and the benefit of U.S. Application No. 63/248,634, filed on Sep. 27, 2021, the entire contents of all of which are incorporated herein by reference.

BACKGROUND

Thyroid hormones are critical for normal growth and development and for maintaining metabolic homeostasis. Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol, bone, muscle, and behavior.

The development of thyroid hormone analogs which avoid the undesirable effects of hyperthyroidism and hypothyroidism while maintaining the beneficial effects of thyroid hormones would open new avenues of treatment for patients with metabolic disease such as obesity, hyperlipidemia, hypercholesterolemia, diabetes and other disorders and diseases such as liver steatosis and non-alcoholic steatohepatitis (NASH), atherosclerosis, cardiovascular diseases, hypothyroidism, thyroid cancer, thyroid diseases, resistance to thyroid hormone and related disorders and diseases.

Subjects with NASH may also experience elevated liver volumes, which can be attributed to increased liver fat and fluid retention due to inflammatory processes in NASH. As NASH progresses to cirrhosis, liver fat decreases as the liver becomes increasingly fibrotic. Liver volume remains elevated in cirrhotic subjects due to ongoing inflammation and venous congestion associated with portal hypertension. Reducing liver volume in cirrhotic subjects is important for maintaining perfusion of the diseased liver and reversing disease progression. Liver volume reduction in NASH and cirrhosis is associated with histopathologic improvement of the liver.

Obesity is a common characteristic of both NASH and cirrhosis, due to insufficient weight loss through diet and lifestyle modifications, this patient population is often prescribed interventional surgical procedures (e.g. bariatric surgery). Liver volume reduction immediately prior to surgery is aggressively pursued to improve surgical access to the stomach.

SUMMARY

In some aspects, the present disclosure provides a method of reducing liver volume in a subject, the method comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use for reducing liver volume in a subject.

In some aspects, the present disclosure provides use of resmetirom, a prodrug thereof, or a pharmaceutically acceptable salt of the resmetirom or the resmetirom prodrug in the manufacture of a medicament for reducing liver volume in a subject.

In some aspects, the present disclosure provides a method of treating or preventing a disease, disorder, or condition in a subject, comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in treating or preventing a disease, disorder, or condition in a subject.

In some aspects, the present disclosure provides use of resmetirom, a prodrug thereof, or a pharmaceutically acceptable salt of the resmetirom or the resmetirom prodrug in the manufacture of a medicament for treating or preventing a disease, disorder, or condition in a subject.

In some embodiments, the disease, disorder, or condition is obesity, hyperlipidemia, hypercholesterolemia, diabetes, non-alcoholic steatohepatitis (NASH), fatty liver, bone disease, thyroid axis alteration, atherosclerosis, cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

In some aspects, the present disclosure provides a method of treating or preventing NASH (e.g., cirrhotic NASH) in a subject, the method comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in treating or preventing NASH (e.g., cirrhotic NASH) in a subject.

In some aspects, the present disclosure provides use of resmetirom, a prodrug thereof, or a pharmaceutically acceptable salt of the resmetirom or the resmetirom prodrug in the manufacture of a medicament for treating or preventing NASH (e.g., cirrhotic NASH) in a subject.

In some aspects, the present disclosure provides a method of treating or preventing portal hypertension in a subject, the method comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in treating or preventing portal hypertension in a subject.

In some aspects, the present disclosure provides use of resmetirom, a prodrug thereof, or a pharmaceutically acceptable salt of the resmetirom or the resmetirom prodrug in the manufacture of a medicament for treating or preventing portal hypertension in a subject.

In some aspects, the present disclosure provides a method of conditioning a subject having a disease, disorder, or condition for a surgery (e.g., bariatric surgery), comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in conditioning a subject having a disease, disorder, or condition for a surgery (e.g., bariatric surgery).

In some aspects, the present disclosure provides use of resmetirom, a prodrug thereof, or a pharmaceutically acceptable salt of the resmetirom or the resmetirom prodrug in the manufacture of a medicament for conditioning a subject having a disease, disorder, or condition for a surgery (e.g., bariatric surgery).

BRIEF DESCRIPTION OF THE DRAWINGS

The above and further features will be more clearly appreciated from the following detailed description when taken in conjunction with the accompanying drawings.

DETAILED DESCRIPTION

Methods and Uses of Resmetirom

Figure 1:
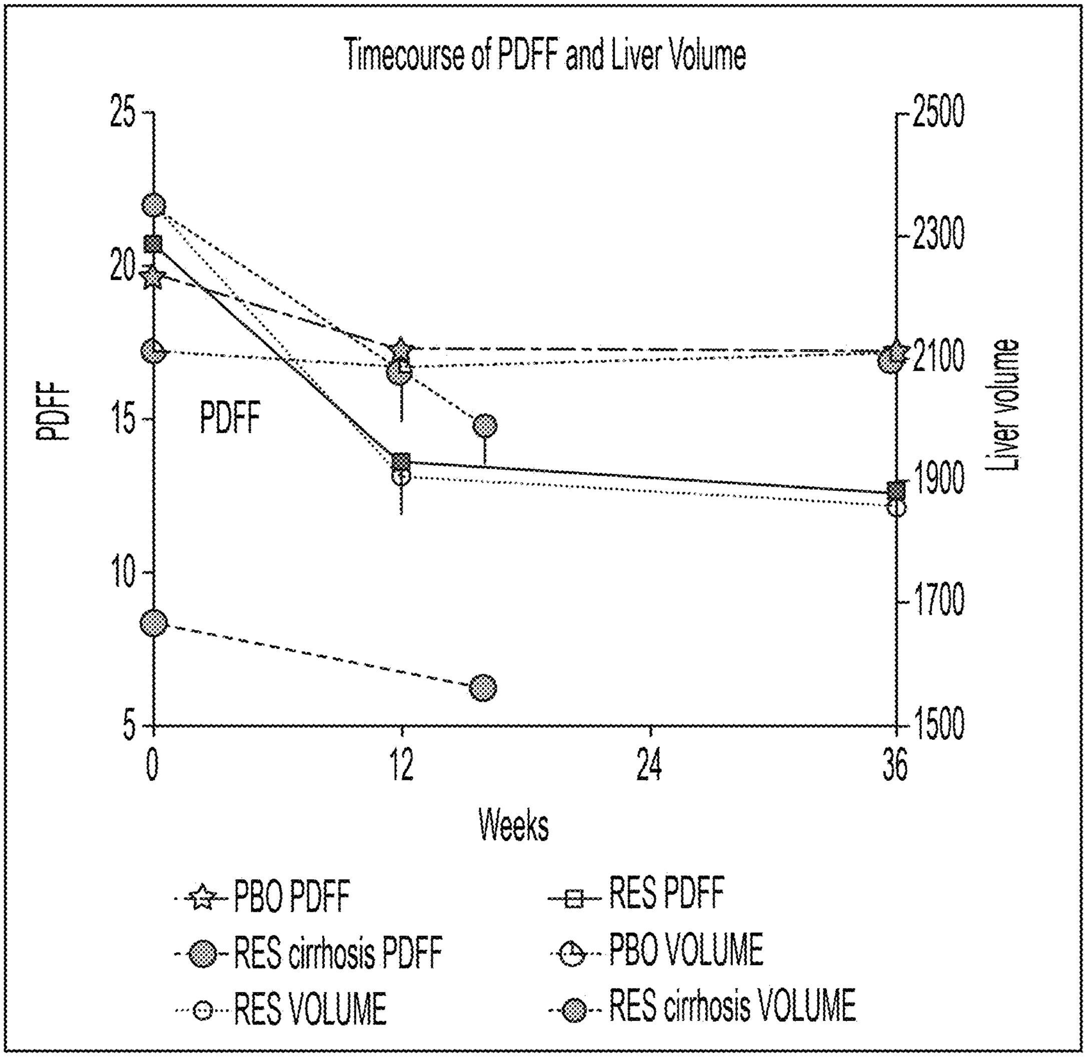
FIG. 1 is a graph showing the correlation of liver volume reduction and proton density fat fraction (PDFF) reduction in placebo and resmetirom treated patients at 12 weeks. "PBO" represents placebo patients and "RES" represents resmetirom-treated patients.

In some aspects, the present disclosure provides a method of reducing liver volume in a subject, the method comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use for reducing liver volume in a subject.

In some aspects, the present disclosure provides use of resmetirom, a prodrug thereof, or a pharmaceutically acceptable salt of the resmetirom or the resmetirom prodrug in the manufacture of a medicament for reducing liver volume in a subject.

In some aspects, the present disclosure provides a method of treating or preventing a disease, disorder, or condition in a subject, comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in treating or preventing a disease, disorder, or condition in a subject.

In some aspects, the present disclosure provides use of resmetirom, a prodrug thereof, or a pharmaceutically acceptable salt of the resmetirom or the resmetirom prodrug in the manufacture of a medicament for treating or preventing a disease, disorder, or condition in a subject.

In some embodiments, the disease, disorder, or condition is obesity, hyperlipidemia, hypercholesterolemia, diabetes, non-alcoholic steatohepatitis (NASH), fatty liver, bone disease, thyroid axis alteration, atherosclerosis, cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

In some aspects, the present disclosure provides a method of treating or preventing NASH (e.g., cirrhotic NASH) in a subject, the method comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in treating or preventing NASH (e.g., cirrhotic NASH) in a subject.

In some aspects, the present disclosure provides use of resmetirom, a prodrug thereof, or a pharmaceutically acceptable salt of the resmetirom or the resmetirom prodrug in the manufacture of a medicament for treating or preventing NASH (e.g., cirrhotic NASH) in a subject.

In some aspects, the present disclosure provides a method of treating or preventing portal hypertension in a subject, the method comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in treating or preventing portal hypertension in a subject.

In some aspects, the present disclosure provides use of resmetirom, a prodrug thereof, or a pharmaceutically acceptable salt of the resmetirom or the resmetirom prodrug in the manufacture of a medicament for treating or preventing portal hypertension in a subject.

In some aspects, the present disclosure provides a method of conditioning a subject having a disease, disorder, or condition for a surgery (e.g., bariatric surgery), comprising administering to the subject resmetirom, a prodrug thereof, or a pharmaceutically acceptable salt of the resmetirom or the resmetirom prodrug (e.g., in a therapeutically effective amount).

In some aspects, the present disclosure provides resmetirom, a prodrug thereof, or a pharmaceutically acceptable salt of the resmetirom or the resmetirom prodrug for use in conditioning a subject having a disease, disorder, or condition for a surgery (e.g., bariatric surgery).

In some aspects, the present disclosure provides use of resmetirom, a prodrug thereof, or a pharmaceutically acceptable salt of the resmetirom or the resmetirom prodrug in the manufacture of a medicament for conditioning a subject having a disease, disorder, or condition for a surgery (e.g., bariatric surgery).

Diseases, Disorders, and Conditions of Subjects

In some embodiments, the subject is human.

In some embodiments, the subject is cirrhotic (e.g., the subject has cirrhosis).

In some embodiments, the subject is non-cirrhotic (e.g., the subject does not have cirrhosis).

In some embodiments, the subject has an amount of liver fat characterized by no more than 5% PDFF.

In some embodiments, the subject has an amount of liver fat characterized by more than 5% PDFF.

In some embodiments, the disease, disorder, or condition is NASH.

In some embodiments, the disease, disorder, or condition is cirrhotic or non-cirrhotic NASH.

In some embodiments, the disease, disorder, or condition is cirrhotic NASH (e.g., NASH associated with cirrhosis).

In some embodiments, the disease, disorder, or condition is liver inflammation.

In some embodiments, the disease, disorder, or condition is associated with an increased liver volume.

In some embodiments, the disease, disorder, or condition is portal hypertension.

In some embodiments, the subject has a liver volume being at least about 5% greater, at least about 10% greater, at least about 20% greater, at least about 30% greater, at least about 40% greater, at least about 50% greater, at least about 60% greater, at least about 70% greater, at least about 80% greater, at least about 90% greater, at least about 100% greater, at least about 150% greater, or at least about 200% greater, as compared to a comparable subject without the disease, disorder, or condition (e.g., without NASH (e.g., without cirrhotic NASH)).

In some embodiments, the subject has a liver fat amount (e.g., as measured by proton density fat fraction (PDFF)) being at least about 5% greater, at least about 10% greater, at least about 20% greater, at least about 30% greater, at least about 40% greater, at least about 50% greater, at least about 60% greater, at least about 70% greater, at least about 80% greater, at least about 90% greater, at least about 100% greater, at least about 150% greater, or at least about 200% greater, as compared to a comparable subject without the disease, disorder, or condition (e.g., without NASH (e.g., without cirrhotic NASH)).

In some embodiments, the subject has a liver fat amount (e.g., as measured by proton density fat fraction (PDFF)) being at most about 200% greater, at most about 150% greater, at most about 100% greater, at most about 90% greater, at most about 80% greater, at most about 70% greater, at most about 60% greater, at most about 50% greater, at most about 40% greater, at most about 30% greater, at most about 20% greater, at most about 10% greater, or at most about 5% greater, as compared to a comparable subject without the disease, disorder, or condition (e.g., without NASH (e.g., without cirrhotic NASH)).

In some embodiments, the subject has a liver fat amount (e.g., as measured by proton density fat fraction (PDFF)) being about 50% or less, about 40% or less, about 30% or less, about 25% or less, about 20% or less, about 15% or less, about 10% or less, about 5% or less, about 4% or less, about 3% or less, about 2% or less, or about 1% or less.

In some embodiments, the subject has a liver fat amount (e.g., as measured by proton density fat fraction (PDFF)) being about 5% or less.

In some embodiments, the subject has a liver fat amount (e.g., as measured by proton density fat fraction (PDFF)) greater than about 5%, greater than about 10%, greater than about 15%, greater than about 20%, greater than about 25%, greater than about 30%, greater than about 40%, greater than about 50%, or greater than about 60%.

In some embodiments, the subject has a liver fat amount (e.g., as measured by proton density fat fraction (PDFF)) being greater than about 5%.

In some embodiments, the subject has a spleen volume being at least about 5% greater, at least about 10% greater, at least about 20% greater, at least about 30% greater, at least about 40% greater, at least about 50% greater, at least about 60% greater, at least about 70% greater, at least about 80% greater, at least about 90% greater, at least about 100% greater, at least about 150% greater, or at least about 200% greater, as compared to a comparable subject without the disease, disorder, or condition (e.g., without portal hypertension).

Administrations of Resmetirom

In some embodiments, the resmetirom, the prodrug thereof, or the pharmaceutically acceptable salt of the resmetirom or the resmetirom prodrug is administered to the subject.

In some embodiments, a pharmaceutical composition comprising the resmetirom, the prodrug thereof, or the pharmaceutically acceptable salt of the resmetirom or the resmetirom prodrug is administered to the subject.

In some embodiments, the resmetirom, the prodrug thereof, or the pharmaceutically acceptable salt of the resmetirom or the resmetirom prodrug is administered to the subject by oral administration.

In some embodiments, the resmetirom, the prodrug thereof, or the pharmaceutically acceptable salt of the resmetirom or the resmetirom prodrug is administered daily.

In some embodiments, the resmetirom, the prodrug thereof, or the pharmaceutically acceptable salt of the resmetirom or the resmetirom prodrug is administered once or twice daily.

In some embodiments, the resmetirom, the prodrug thereof, or the pharmaceutically acceptable salt of the resmetirom or the resmetirom prodrug is administered once daily.

In some embodiments, the resmetirom, the prodrug thereof, or the pharmaceutically acceptable salt of the resmetirom or the resmetirom prodrug is administered to the subject at a daily dosage of from about 10 to about 250 mg, from about 20 to about 200 mg, from about 20 to about 150 mg, from about 20 to about 100 mg, from about 50 to about 200 mg, or from about 50 to about 150 mg.

In some embodiments, the resmetirom, the prodrug thereof, or the pharmaceutically acceptable salt of the resmetirom or the resmetirom prodrug is administered to the subject at a daily dosage of about 5 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 500 mg, or about 1000 mg.

In some embodiments, the resmetirom, the prodrug thereof, or the pharmaceutically acceptable salt of the resmetirom or the resmetirom prodrug is administered to the subject at a daily dosage of about 60±20 mg, about 60±15 mg, about 60±10 mg, about 60±5 mg, about 60±4 mg, about 60±3 mg, about 60±2 mg, or about 60±1 mg (e.g., about 60 mg).

In some embodiments, the resmetirom, the prodrug thereof, or the pharmaceutically acceptable salt of the resmetirom or the resmetirom prodrug is administered to the subject at a daily dosage of about 60 mg.

In some embodiments, the resmetirom, the prodrug thereof, or the pharmaceutically acceptable salt of the resmetirom or the resmetirom prodrug is administered to the subject at a daily dosage of about 80±20 mg, about 80±15 mg, about 80±10 mg, about 80±5 mg, about 80±4 mg, about 80±3 mg, about 80±2 mg, or about 80±1 mg (e.g., about 80 mg).

In some embodiments, the resmetirom, the prodrug thereof, or the pharmaceutically acceptable salt of the resmetirom or the resmetirom prodrug is administered to the subject at a daily dosage of about 80 mg.

In some embodiments, the resmetirom, the prodrug thereof, or the pharmaceutically acceptable salt of the resmetirom or the resmetirom prodrug is administered to the subject at a daily dosage of about 100±20 mg, about 100±15 mg, about 100±10 mg, about 100±5 mg, about 100±4 mg, about 100±3 mg, about 100±2 mg, or about 100±1 mg (e.g., about 100 mg).

In some embodiments, the resmetirom, the prodrug thereof, or the pharmaceutically acceptable salt of the resmetirom or the resmetirom prodrug is administered to the subject at a daily dosage of about 100 mg.

In some embodiments, the resmetirom, the prodrug thereof, or the pharmaceutically acceptable salt of the resmetirom or the resmetirom prodrug is administered without any drug holiday.

In some embodiments, the resmetirom, the prodrug thereof, or the pharmaceutically acceptable salt of the resmetirom or the resmetirom prodrug is administered with one or more drug holidays.

In some embodiments, the resmetirom, the prodrug thereof, or the pharmaceutically acceptable salt of the resmetirom or the resmetirom prodrug is administered for about one week, about two weeks, about three weeks, about four weeks, about five weeks, about six weeks, about seven weeks, about eight weeks, about nine weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the resmetirom, the prodrug thereof, or the pharmaceutically acceptable salt of the resmetirom or the resmetirom prodrug is administered for longer than about 52 weeks.

Potential Results of Administrations

In some embodiments, the administration eliminates, or reduces the severity of, the disease, disorder, or condition.

In some embodiments, the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60% (e.g., over a period of 12 weeks or 52 weeks).

In some embodiments, the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60%, over a period of 12 weeks.

In some embodiments, the administration reduces the liver volume by at least about 10% over a period of 12 weeks.

In some embodiments, the administration reduces the liver volume by at least about 15% over a period of 12 weeks.

In some embodiments, the administration reduces the liver volume by at least about 20% over a period of 12 weeks.

In some embodiments, the administration reduces the liver volume by at least about 25% over a period of 12 weeks.

In some embodiments, the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60%, over a period of 52 weeks.

In some embodiments, the administration reduces the liver volume by at least about 10% over a period of 52 weeks.

In some embodiments, the administration reduces the liver volume by at least about 15% over a period of 52 weeks.

In some embodiments, the administration reduces the liver volume by at least about 20% over a period of 52 weeks.

In some embodiments, prior to the administration the subject has a liver fat amount (e.g., as measured by MRI-PDFF) being about 5% or less, and the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60% (e.g., over a period of 12 weeks or 52 weeks).

In some embodiments, prior to the administration the subject has a liver fat amount (e.g., as measured by MRI-PDFF) being about 5% or less, and the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60%, over a period of 12 weeks.

In some embodiments, prior to the administration the subject has a liver fat amount (e.g., as measured by MRI-PDFF) being about 5% or less, and the administration reduces the liver volume by at least about 10% over a period of 12 weeks.

In some embodiments, prior to the administration the subject has a liver fat amount (e.g., as measured by MRI-PDFF) being about 5% or less, and the administration reduces the liver volume by at least about 15% over a period of 12 weeks.

In some embodiments, prior to the administration the subject has a liver fat amount (e.g., as measured by MRI-PDFF) being about 5% or less, and the administration reduces the liver volume by at least about 20% over a period of 12 weeks.

In some embodiments, prior to the administration the subject has a liver fat amount (e.g., as measured by MRI-PDFF) being about 5% or less, and the administration reduces the liver volume by at least about 25% over a period of 12 weeks.

In some embodiments, prior to the administration the subject has a liver fat amount (e.g., as measured by MRI-PDFF) being about 5% or less, and the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60%, over a period of 52 weeks.

In some embodiments, prior to the administration the subject has a liver fat amount (e.g., as measured by MRI-PDFF) being about 5% or less, and the administration reduces the liver volume by at least about 10% over a period of 52 weeks.

In some embodiments, prior to the administration the subject has a liver fat amount (e.g., as measured by MRI-PDFF) being about 5% or less, and the administration reduces the liver volume by at least about 15% over a period of 52 weeks.

In some embodiments, prior to the administration the subject has a liver fat amount (e.g., as measured by MRI-PDFF) being about 5% or less, and the administration reduces the liver volume by at least about 20% over a period of 52 weeks.

In some embodiments, the administration reduces the liver fat amount (e.g., as measured by MRI-PDFF) by about 60% or less, about 50% or less, about 45% or less, about 40% or less, about 35% or less, about 30% or less, about 25% or less, about 20% or less, about 15% or less, about 10% or less, or about 5% or less, as compared to the liver fat amount of the subject prior to the administration.

In some embodiments, prior to the administration the subject has a liver fat amount (e.g., as measured by MRI-PDFF) being about 5% or less, and the administration reduces the liver fat amount (e.g., as measured by MRI-PDFF) by about 60% or less, about 50% or less, about 45% or less, about 40% or less, about 35% or less, about 30% or less, about 25% or less, about 20% or less, about 15% or less, about 10% or less, or about 5% or less, as compared to the liver fat amount of the subject prior to the administration.

In some embodiments, the administration reduces the liver fat amount (e.g., as measured by MRI-PDFF) by about 20% or less, about 15% or less, about 10% or less, about 5% or less, about 4% or less, about 3% or less, about 2% or less, or about 1% or less, as compared to the liver volume of the subject prior to the administration.

In some embodiments, prior to the administration the subject has a liver fat amount (e.g., as measured by MRI-PDFF) being about 5% or less; the administration reduces the liver fat amount (e.g., as measured by MRI-PDFF) by about 60% or less, about 50% or less, about 45% or less, about 40% or less, about 35% or less, about 30% or less, about 25% or less, about 20% or less, about 15% or less, about 10% or less, or about 5% or less, as compared to the liver fat amount of the subject prior to the administration; and the administration reduces the liver volume by at least about 5%, at least about 10%, at least about 15%, at least about 20%, at least about 25%, at least about 30%, at least about 35%, at least about 40%, at least about 45%, at least about 50%, at least about 55%, or at least about 60% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 40% or less, as compared to the liver fat amount of the subject prior to the administration; and the administration reduces the liver volume by at least about 10% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 35% or less, as compared to the liver fat amount of the subject prior to the administration; and the administration reduces the liver volume by at least about 10% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 30% or less, as compared to the liver fat amount of the subject prior to the administration; and the administration reduces the liver volume by at least about 10% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 40% or less, as compared to the liver fat amount of the subject prior to the administration; and the administration reduces the liver volume by at least about 15% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 35% or less, as compared to the liver fat amount of the subject prior to the administration; and the administration reduces the liver volume by at least about 15% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 30% or less, as compared to the liver fat amount of the subject prior to the administration; and the administration reduces the liver volume by at least about 15% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 40% or less, as compared to the liver fat amount of the subject prior to the administration; and the administration reduces the liver volume by at least about 20% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 35% or less, as compared to the liver fat amount of the subject prior to the administration; and the administration reduces the liver volume by at least about 20% (e.g., over a period of 12 weeks or 52 weeks).

In some embodiments, prior to the administration the subject has a liver fat amount (e.g., as measured by MRI-PDFF) being about 5% or less; the administration reduces the liver fat amount (e.g., as measured by MRI-PDFF) by about 30% or less, as compared to the liver fat amount of the subject prior to the administration; and the administration reduces the liver volume by at least about 20% (e.g., over a period of 12 weeks or 52 weeks).

In some embodiments, the liver volume reduction is dependent from the liver fat amount (e.g., the liver fat amount prior to the administration).

In some embodiments, the liver volume reduction is independent from the liver fat amount (e.g., the liver fat amount prior to the administration).

In some embodiments, the liver volume reduction is dependent from the liver fat amount reduction.

In some embodiments, the liver volume reduction is independent from the liver fat amount reduction.

In some embodiments, the liver volume reduction is greater than the liver fat amount reduction.

In some embodiments, the liver volume reduction is at least about 5% greater, at least about 10% greater, at least about 20% greater, at least about 30% greater, at least about 40% greater, at least about 50% greater, at least about 60% greater, at least about 70% greater, at least about 80% greater, at least about 90% greater, at least about 100% greater, at least about 150% greater, at least about 200% greater, at least about 300% greater, at least about 400% greater, at least about 500% greater, at least about 600% greater, at least about 700% greater, at least about 800% greater, at least about 900% greater, at least about 1000%, as compared to the liver fat amount reduction.

In some embodiments, the administration eliminates, or reduces the severity of, liver inflammation.

In some embodiments, the administration eliminates, or reduces the severity of, portal hypertension.

In some embodiments, the administration reduces the blood pressure in the portal vein of the subject.

In some embodiments, the administration reduces the blood pressure in the portal vein of the subject by at least about 5%, at least about 10%, at least about 15%, at least about 20%, at least about 25%, at least about 30%, at least about 35%, at least about 40%, at least about 45%, at least about 50%, at least about 55%, or at least about 60% (e.g., over a period of 12 weeks or 52 weeks).

In some embodiments, the administration reduces the spleen volume of the subject.

In some embodiments, the administration reduces the spleen volume by at least about 5%, at least about 10%, at least about 15%, at least about 20%, at least about 25%, at least about 30%, at least about 35%, at least about 40%, at least about 45%, at least about 50%, at least about 55%, or at least about 60% (e.g., over a period of 12 weeks or 52 weeks).

In some embodiments, the administration reduces the spleen volume by at least about 10% or at least about 15% (e.g., over a period of 12 weeks or 52 weeks).

In some embodiments, the administration reduces the spleen volume by at least about 10% or at least about 15% over a period of 12 weeks.

In some embodiments, the administration reduces the spleen volume by at least about 10% or at least about 15% over a period of 52 weeks.

Other Aspects

In some embodiments, the liver disease or disorder treated by the methods of the present disclosure is fatty liver disease.

In some embodiments, the liver disease or disorder treated by the methods of the present disclosure is nonalcoholic fatty liver disease (NAFLD). Two types of NAFLD are simple fatty liver and NASH. NAFLD refers to a wide spectrum of liver diseases ranging from simple fatty liver (steatosis), to NASH, to cirrhosis. All of the stages of NAFLD have in common the accumulation of fat in the hepatocytes. NASH is a form of NAFLD in which the subject also has hepatitis. More specifically in NASH, the fat accumulation is associated with varying degrees of inflammation (hepatitis) and scarring (fibrosis) of the liver. NAFLD and NASH occur in individuals who do not consume excessive amounts of alcohol. Yet, in many respects, the histological picture of an NAFLD biopsy is similar to what can be seen in liver disease caused by alcohol abuse. NAFLD and NASH are considered the primary fatty liver diseases. The secondary fatty liver diseases include those that occur in other types of liver disease. Thus, alcoholic liver disease (ALD) is the most frequent secondary fatty liver disease. Secondary fatty liver can also occur in chronic viral hepatitis C (HCV), chronic viral hepatitis B (HBV), chronic autoimmune hepatitis (AIH), and Wilson's disease.

In some embodiments, the liver disease or disorder treated by the methods of the present disclosure is NASH.

In some embodiments, the lipid disease or disorder treated by the methods of the present disclosure is dyslipidemia, hyperlipidemia, hypertriglyceridemia, hypercholesterolemia, low HDL, or high LDL. In some embodiments, the hypercholesterolemia is heterozygous familial hypercholesterolemia (HeFH) or homozygous familial hypercholesterolemia (HoFH).

In some embodiments, the subject is a mammal.

In some embodiments, the subject is a human.

Resmetirom, a prodrug thereof, or a pharmaceutically acceptable salt of the resmetirom or the resmetirom prodrug can be formulated into a pharmaceutical composition for administration. The pharmaceutical composition can further comprise a pharmaceutically acceptable carriers or excipient.

The pharmaceutical composition can be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

In some embodiments, the pharmaceutical composition is formulated in a gel.

In some embodiments, the pharmaceutical composition is formulated in a tablet.

In some embodiments, the pharmaceutical composition is formulated in a pill.

In some embodiments, the pharmaceutical composition is formulated in a capsule.

In some embodiments, the pharmaceutical composition is formulated in a solution.

EXEMPLARY EMBODIMENTS

Exemplary Embodiment No. 1. A method of reducing liver volume in a cirrhotic or non-cirrhotic subject with non-alcoholic steatohepatitis (NASH), the method comprising administering to the subject a therapeutically effective amount of resmetirom.

Exemplary Embodiment No. 2. The method of Exemplary Embodiment 1, wherein the subject is non-cirrhotic.

Exemplary Embodiment No. 3. The method of Exemplary Embodiment 1, wherein the subject is cirrhotic.

Exemplary Embodiment No. 4. The method of any one of the preceding Exemplary Embodiments, wherein the liver volume is reduced by at least about 10% within a treatment period of 12 weeks.

Exemplary Embodiment No. 5. The method of any one of the preceding Exemplary Embodiments, wherein the liver volume is reduced by at least about 15% within a treatment period of 12 weeks.

Exemplary Embodiment No. 6. The method of any one of the preceding Exemplary Embodiments, wherein the therapeutically effective amount of resmetirom is about 5 to 300 mg.

Exemplary Embodiment No. 7. The method of any one of Exemplary Embodiments 1-6, wherein the therapeutically effective amount of resmetirom is about 60 mg.

Exemplary Embodiment No. 8. The method of any one of Exemplary Embodiments 1-6, wherein the therapeutically effective amount of resmetirom is about 80 mg.

Exemplary Embodiment No. 9. The method of any one of Exemplary Embodiments 1-6, wherein the therapeutically effective amount of resmetirom is about 100 mg.

Exemplary Embodiment No. 10. The method of any one of the preceding Exemplary Embodiments, wherein resmetirom is administered daily.

Exemplary Embodiment No. 11. The method of any one of the preceding Exemplary Embodiments, wherein resmetirom is administered once daily.

Exemplary Embodiment No. 12. The method of any one of the preceding Exemplary Embodiments, wherein the subject has an amount of liver fat characterized by no more than 5% PDFF.

Exemplary Embodiment No. 13. A method of treating NASH in a cirrhotic subject in need thereof, the method comprising administering to the subject a therapeutically effective amount of resmetirom.

Exemplary Embodiment No. 14. The method of Exemplary Embodiment 13, wherein the therapeutically effective amount of resmetirom is about 5 to 300 mg.

Exemplary Embodiment No. 15. The method of Exemplary Embodiment 13, wherein the therapeutically effective amount of resmetirom is about 60 mg.

Exemplary Embodiment No. 16. The method of Exemplary Embodiment 13, wherein the therapeutically effective amount of resmetirom is about 80 mg.

Exemplary Embodiment No. 17. The method of Exemplary Embodiment 13, wherein the therapeutically effective amount of resmetirom is about 100 mg.

Exemplary Embodiment No. 18. The method of Exemplary Embodiment 13, wherein resmetirom is administered daily.

Exemplary Embodiment No. 19. The method of Exemplary Embodiment 13, wherein resmetirom is administered once daily.

Exemplary Embodiment No. 20. The method of any one of Exemplary Embodiments 13-19, wherein the subject has an amount of liver fat characterized by no more than 5% PDFF.

Definitions

Unless otherwise defined, all technical and scientific terms used herein have the same meaning as commonly understood by one of ordinary skill in the art to which this disclosure belongs. The terminology used in the description is intended to describe particular embodiments only, and is not intended to limit the scope of the invention.

Where a range of values is provided, it is understood that the range includes both of the endpoints with that range, as well as all intervening values.

The articles "a" and "an" as used herein and in the appended claims are used herein to refer to one or to more than one (i.e., to at least one) of the grammatical object of the article unless the context clearly indicates otherwise. By way of example, "an ultrapure form" means one ultrapure form or more than one ultrapure form.

The phrase "and/or," as used herein in the specification and in the claims, should be understood to mean "either or both". Other elements may optionally be present other than the elements specifically identified by the "and/or" clause. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

Unless explicitly indicated otherwise, the terms "approximately" and "about" are synonymous. In some embodiments, "approximately" and "about" refer to the recited amount, value, dose or duration ±10%, ±8%, ±6%, ±5%, ±4%, ±2%, ±1%, or ±0.5%. In some embodiments, "approximately" and "about" refer to the listed amount, value, dose, or duration ±5%. In some embodiments, "approximately" and "about" refer to the listed amount, value, dose, or duration ±2%. In some embodiments, "approximately" and "about" refer to the listed amount, value, dose, or duration ±1%.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the term "MRI-PDFF" describes proton-density-fat-fraction determined by a magnetic resonance imaging (MRI)-based determination. MRI-PDFF is an MRI-based diagnostic imaging biomarker of the liver, developed in order to facilitate, by enriching, patient recruitment for clinical trials in NASH. MRI-PDFF is a measure to assess liver fat content and is proposed to be used as non-invasive method to limit unnecessary liver biopsies by avoiding biopsies in those patients with a low likelihood of fatty liver. It is intended to be used as a pre-screening strategy in an adult population having clinical signs or risk factors suggesting non-alcoholic fatty liver disease (NAFLD). MRI-PDFF is an accurate quantitative imaging biomarker with high repeatability and reproducibility and has provided results from test and validation datasets with MRI-PDFF compared to liver histology to show optimal MRI-PDFF cut-offs in order to reduce the number of unnecessary biopsies prior to enrolment in clinical trials and identify candidates who are most likely to meet the criteria for enrolment in NASH clinical trials.

As used herein, the term "portal hypertension", refers to an increase in the pressure within the portal vein (the vein that carries blood from the digestive organs (large and small intestines, stomach, pancreas, spleen) to the liver). The increase in pressure is caused by a blockage in the blood flow through the liver.

As used herein, the term "cirrhosis", refers to a late stage of scarring (fibrosis) of the liver caused by many forms of liver diseases and conditions, such as hepatitis and chronic alcoholism. The liver fat of a cirrhosis subject (e.g., as measured by MRI-PDFF) is no more than 5%.

As used herein, the term "preventing" or "prevent" describes reducing or eliminating the onset of the symptoms or complications of such disease, condition or disorder.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "dosage" or "daily dosage" refers to the weight of the resmetirom, the prodrug thereof, or the pharmaceutically acceptable salt of the resmetirom or the resmetirom prodrug.

As used herein, the term "pharmaceutically acceptable excipient" means an excipient that is useful in preparing a formulation that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the term "subject" includes human and non-human mammal, as well as cell lines, cell culture, tissues, and organs. In some embodiments, the subject is a mammal. The mammal can be e.g., a human or appropriate non-human mammal, such as primate, mouse, rat, dog, cat, cow, horse, goat, camel, sheep or a pig. In some embodiments, the subject is a human.

As used herein, the term "subject in need thereof", refers to a subject having a disease (to be treated) or having an increased risk of developing the disease (to be prevented). A subject in need thereof can be one who has been previously diagnosed or identified as having a disease or disorder disclosed herein. A subject in need thereof can also be one who has (e.g., is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that doesn't respond or hasn't yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

It is to be understood that resmetirom, a prodrug thereof, or a pharmaceutically acceptable salt of the resmetirom or the resmetirom prodrug may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "salt" or "pharmaceutically acceptable salt" refers to a derivative of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc. Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3. It is to be understood that all references to pharmaceutically acceptable salts include solvent addition forms (solvates) or crystal forms (polymorphs) as defined herein, of the same salt.

As used herein, "MGL-3196" is equivalent to "resmetirom," which is equivalent to 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (i.e.,

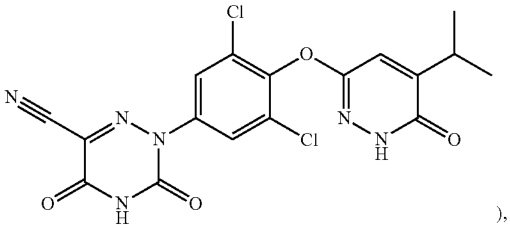 [SMILES: CC(C)c1cc(Oc2c(Cl)cc(-n3nc(C#N)c(=O)[nH]c3=O)cc2Cl)n[nH]c1=O]

), or any of its pharmaceutically acceptable salts or solid forms, such as those disclosed in U.S. Pat. No. 9,266,861 and U.S. application Ser. No. 17/257,070, the contents of each of which are incorporated herein by reference.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Liver Volume Reduction in Resmetirom-treated Non-cirrhotic and Cirrhotic NASH Patients Hepatomegaly may cause symptoms (e.g., pain) in NASH patients, and is thought to be driven primarily by high liver fat content. Resmetirom (MGL-3196) is a liver-directed, orally active, highly selective THR-β agonist in Phase 3 development for the treatment of NASH with significant (stage 2-3) fibrosis. In a 36-week Phase 2 serial MRI-PDFF and liver biopsy study in adults with biopsy-confirmed NASH (NAS≥4, F1-F3) and hepatic fat fraction ≥10%, resmetirom treated patients, compared with placebo, showed statistically significant liver fat reduction that was associated with NASH resolution on liver biopsy. The purpose of this study was to assess the relationship between liver triglycerides as measured by MRI-PDFF and liver volume (LV) in placebo and resmetirom-treated patients.

MRI-PDFF and liver volume (LV) were assessed in, (n=117), and a NASH-cirrhotic active resmetirom treatment arm of MAESTRO-NAFLD-1 (n=73), in patients who had at least baseline and one additional serial PDFF. LV was assessed using a validated artificial intelligence model for segmenting the liver on standard MR images.

LV at baseline was elevated in non-cirrhotic and cirrhotic NASH patients relative to literature values for healthy controls and was greater than predicted even after accounting for sex and body weight. PDFF correlated with LV at baseline in non-cirrhotic ($r2=0.19$, $p<0.001$) and more weakly in cirrhotic NASH ($r2=0.079$, $p=0.01$). Reduction in LV (CFB) correlated with reduction in PDFF in placebo ($r2=0.25$, $p=0.001$) and resmetirom ($r2-0.38$, $p<0.0001$) treated patients at 12 (and 36 (not shown)) weeks (see, e.g., FIG. 1). LV reduction was greater in resmetirom (−18.6% (1.1), −20.5% (1.2) compared to placebo (−0.4% (1.5), 0.1% (1.9) treated at 12 and 36 weeks, respectively ($p<0.0001$). A higher percentage of resmetirom (69.2%) than placebo (5.3%) patients had a ≥15% reduction in liver volume ($p<0.0001$) at Week 12, and similarly at Week 36. The relationship between LV reduction and PDFF reduction was proportionately weaker in placebo compared to resmetirom treated non-cirrhotic NASH patients. In cirrhotic NASH patients treated with resmetirom (see FIG. 1), LV reduction was much greater than expected based on the small reduction in PDFF, especially in patients with PDFF≤5% at baseline (LV mean % CFB, −16.3% versus PDFF, mean % CFB, −2.5% at week 16). Resmetirom treated patients who had NASH resolution and/or fibrosis reduction on biopsy at week 36 all had a PDFF reduction ≥30% and/or LV reduction of ≥15% at week 12.

Without wishing to be bound by theory, reduction in liver volume in resmetirom treated patients may be explained in part by reduction in liver triglycerides (measured by MRI-PDFF), but it also may be driven by other changes related to its mechanism of action. LV reduction may be associated with histopathologic improvement of NASH that may be further assessed by data from Phase 3 MAESTRO-NASH study.

Example 2. Biomarkers, Imaging and Safety in Resmetirom 52 Week Non-Cirrhotic NASH Phase 3 Clinical Trial, Completed Open-Label Arm of MAESTRO-NAFLD-1

MAESTRO-NASH NCT03900429 and MAESTRO-NAFLD-1 NCT04197479 are 52 week Phase 3 registrational double blind placebo controlled clinical trials to study the effect of resmetirom in more than 2,000 NASH patients. A goal of MAESTRO-NAFLD-1, a 1,200 patient "real life" NASH study is to identify non-invasive markers that correlate with patient response to resmetirom treatment. The 169 patient, 100 mg open label (OL) arm completed the 52 week study in July 2021.

Eligibility required at least 3 metabolic risk factors (Metabolic syndrome), fibroscan kilopascals (kPa) consistent with ≥F1 fibrosis stage, and MRI-PDFF≥8%. The primary and key secondary endpoints of MAESTRO-NAFLD-1 including safety, relative percent reduction of MRI-PDFF (week 16), LDL cholesterol (LDL-C) (week 24), apolipoprotein B and triglycerides, fibroscan and 52 week endpoints were analyzed in the OL arm.

Figure 2:
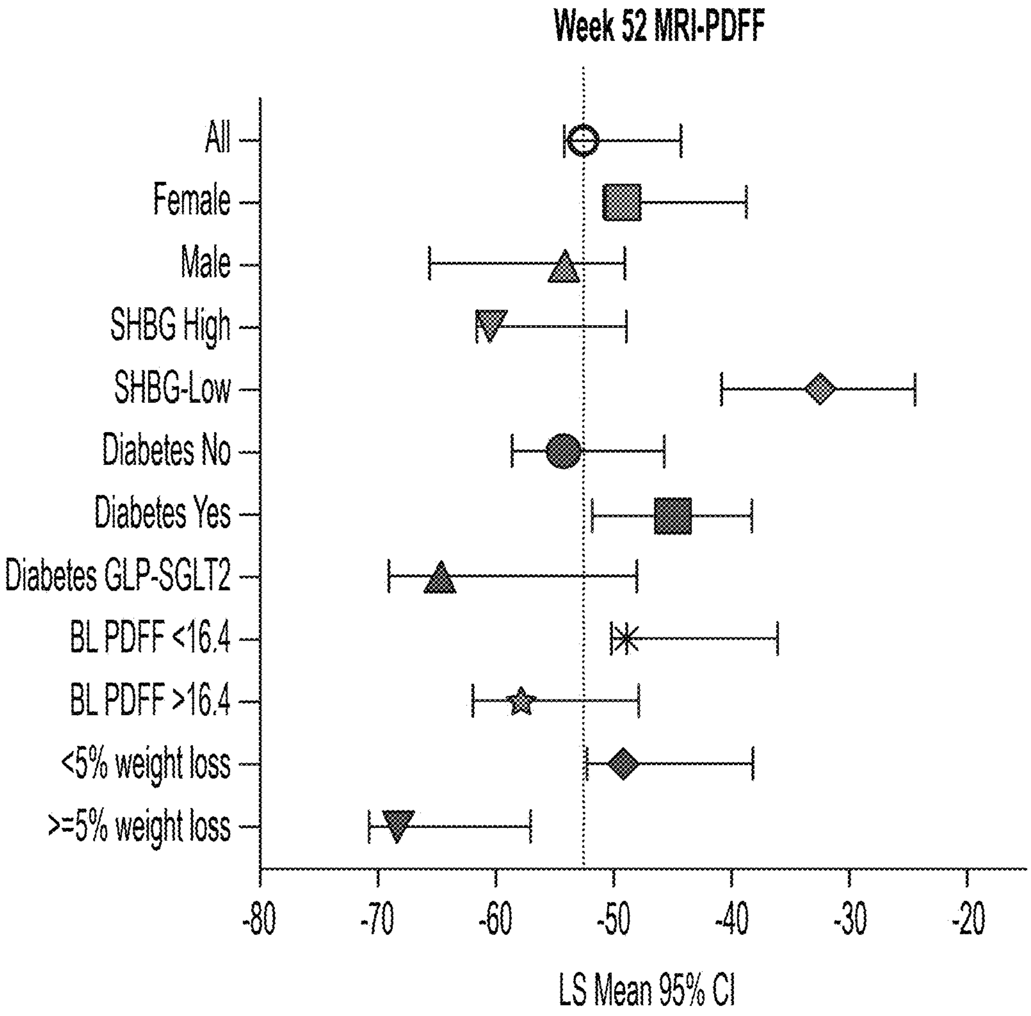
FIG. 2 is a graph showing change in MRI-PDFF in several subgroups of patients treated with 100 mg resmetirom, once daily, for 52 weeks. "High SHBG" corresponds with 2/3 study patients with the highest increase from baseline in sex hormone binding globulin (SHBG), a biomarker for resmetirom liver exposure.
Figure 3:
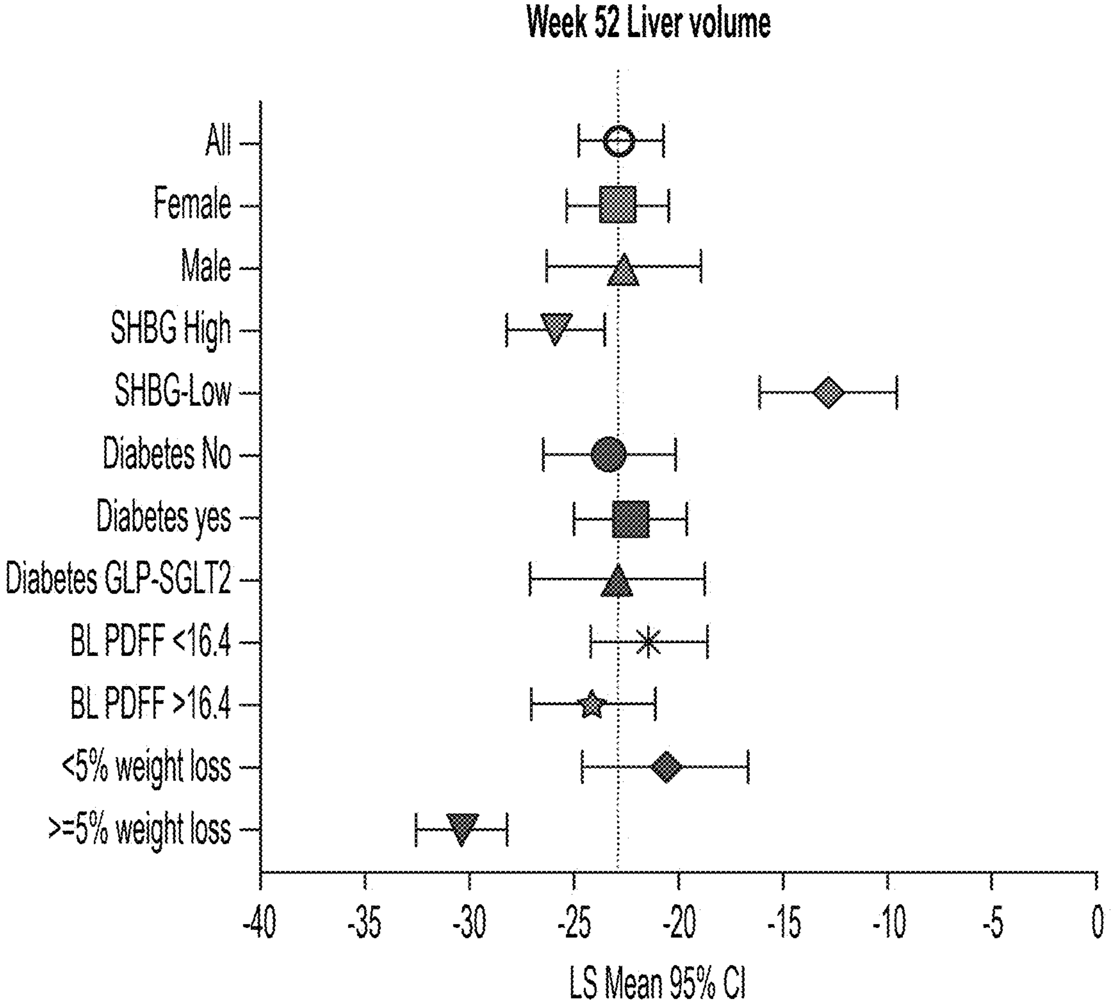
FIG. 3 is a graph showing change in liver volume in several subgroups of patients treated with 100 mg resmetirom, once daily, for 52 weeks. "High SHBG" corresponds with 2/3 study patients with the highest increase from baseline in SHBG, a biomarker for resmetirom liver exposure.

Mean age was 55.7 (11.5 (SD)), female 69%, BMI 35.8 (6.0), diabetes 43%, hypertension 62%, dyslipidemia >70%, ASCVD score 11.5%; fibroscan (kPa 7.7 (3.6)), and MRI-PDFF 17% (7%). Statistically significant ($p<0.0001$) reduction of MRI-PDFF-53% (3.3% (SE)) overall, and in several subgroups were observed at week 52 (see, e.g., FIG. 2). Liver volume (LV) was elevated at baseline (2202 $cm^3$ (535)) by ~50% relative to normal controls and ~15% after correction for BMI (Euro J of Radiol 106, 2018, 32-37). Resmetirom reduced LV-21% (1.0%), −23% (1.0%) respectively, at weeks 16 and 52 ($p<0.0001$), in all demographic groups (see, e.g., FIG. 3). LV reduction was 2-3 fold greater than predicted by % reduction in MRI-PDFF, a measure of liver fat content (Clin Gastroenterol Hepatol. 2015 13:561-

568); LV-corrected mean MRI-PDFF reduction was-63% (2.4%). Weight loss ≥5% occurred in ~25% and was linked to resmetirom exposure (SHBG). At week 52, MRE (−0.34, p=0.03); fibroscan CAP (−39 (4.6)) and VCTE (−1.87; −20%) (p<0.0001) were reduced relative to baseline. LDL-C (−22% (1.9%), apolipoprotein-B (−24% (1.6%)), triglycerides (−24% (2.6) were statistically reduced (p<0.0001). Decreases from baseline in liver enzymes were ALT-20 IU, AST-11 IU, GGT-25 IU (p<0.0001). Significant reductions in inflammatory and fibrosis biomarkers, reverse T3, ELF, and M30, and an increase in adiponectin were observed. No safety flags were identified; Blood pressure (systolic, diastolic) was reduced by ~2 mmHg, (p=0.02); bone mineral density (DEXA) was unchanged at 52 weeks.

In this 52 week Phase 3 OL study, noninvasively identified NASH patients treated with 100 mg per day of resmetirom for up to 52 weeks demonstrated rapid and sustained reduction in (1) hepatic fat and liver volume; (2) fibrosis as assessed by biomarkers, MRE, and fibroscan; (3) LDL and atherogenic lipids; and (4) liver enzymes inflammatory biomarkers, providing support for the use of non-invasive tests to monitor individual NASH patient response to resmetirom treatment.

Example 3. Biomarkers, Imaging and Safety in a Well-Compensated NASH Cirrhotic Cohort Treated with Resmetirom, a Thyroid Hormone Receptor Beta Agonist, for 52 Weeks MAESTRO-NAFLD-1 is a 52-week >1200 patient Phase 3 randomized double blind placebo controlled NASH clinical trial to study safety and biomarker effects of resmetirom, a selective thyroid hormone receptor beta agonist, in NASH patients with F1-F4 fibrosis identified using non-invasive biomarkers and imaging (NCT04197479). A goal of this "real life" NASH study is to identify non-invasive markers that correlate with individual patient response to resmetirom treatment. The study includes an open label active resmetirom treatment arm in well-compensated NASH cirrhotic patients.

Eligibility required at least 3 metabolic risk factors (metabolic syndrome), and NASH cirrhosis diagnosed on liver biopsy or according to accepted criteria. The primary and key secondary end points of the cirrhotic arm include safety, relative percent reduction of MRI-PDFF (week 16), LDL cholesterol (LDL-C) (week 24), Apolipoprotein B and triglycerides, and markers of fibrosis. Patients received 80-100 mg daily dose of resmetirom for 52 weeks.

105 well-compensated NASH cirrhotic patients were enrolled in the open label arm, 2/3 confirmed by liver biopsy. Demographics include mean age 62.7 (9.0 (SD)), female 64%, BMI 35.4 (7.4), diabetes 70%, hypertension 77%, dyslipidemia >70%, mean ASCVD score 16.1%, hypothyroid 32.4%, 51% on statins. MRE kPa, 5.7 (2.1); fibroscan kPa, 24.6 (14.9), CAP, 318 (59) and mean MRI-PDFF, 8.1% (5). Stage of cirrhosis was inversely correlated with baseline PDFF. At week 52 resmetirom lowered fibroscan CAP (−42 units (p<0.0001) and kPa (−7.6 kPa, p=0.02).

Figure 4:
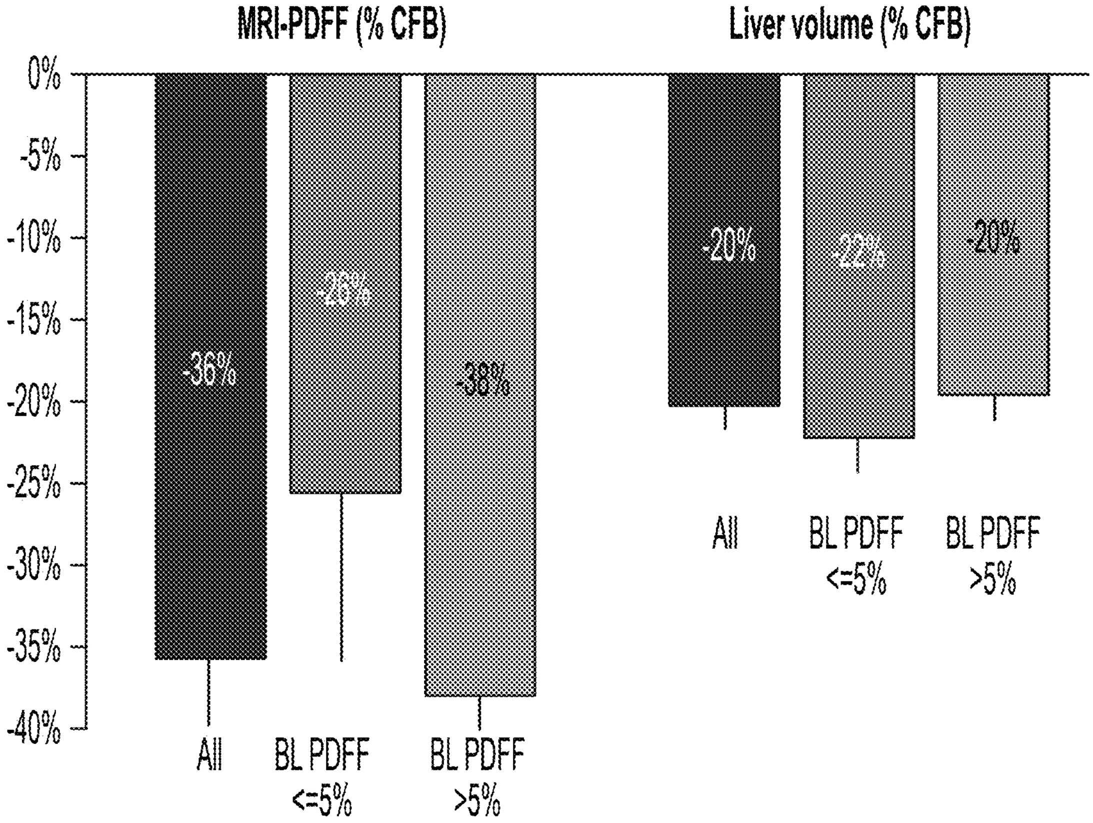
FIG. 4 is a graph showing resmetirom-mediated changes to the MRI-PDFF and liver volume (LV) at week 52.
Figure 5:
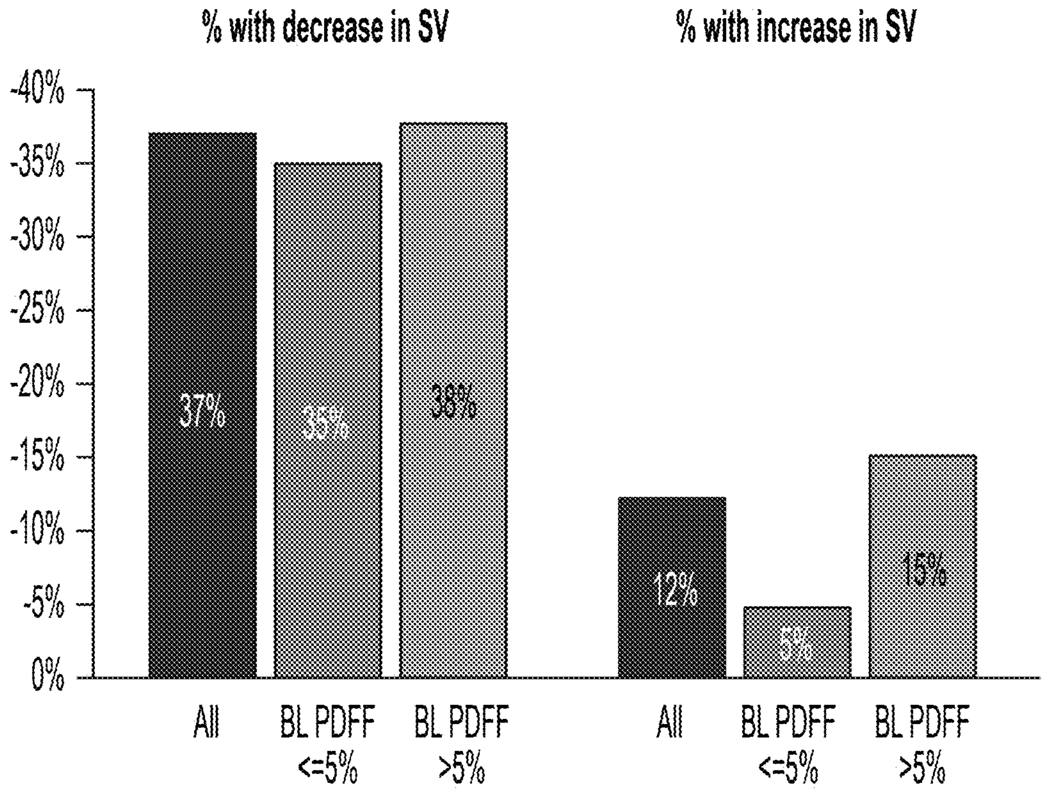
FIG. 5 is a graph showing percentage of patients at week 52 with ≥10% reduction or ≥10% increase in spleen volume (SV).
Figure 6:
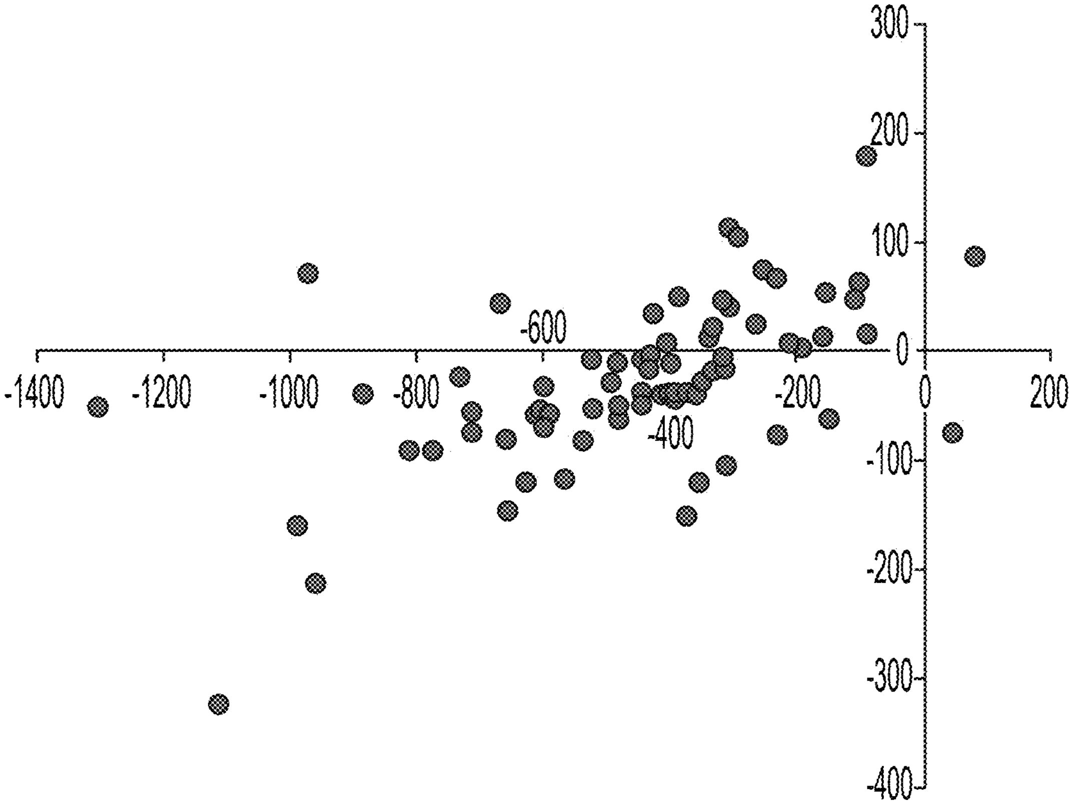
FIG. 6 is a graph showing the correlation between 52 week liver volume change and spleen volume change in patients who entered the study with baseline PDFF<8%.

In patients with baseline PDFF>5% (5%=UL normal), resmetirom lowered PDFF by 37% (p<0.0057). Resmetirom lowered MRE by 0.68 kPa at week 52, and 34% had an MRE reduction of ≥15%. GGT, −27%, p=0.04 and ALP-18%, p=0.04 were reduced. Liver volume (LV), which was elevated in NASH cirrhosis patients at baseline, was reduced-15.9% (7.7%) at week 16 (p<0.0001) independent of baseline PDFF. 73% of patients, independent of baseline cirrhosis severity, had ≥15% reduction in LV at week 52 (see, e.g., FIG. 4). Reduction in PDFF was related to LV reduction only in patients with BL PDFF≥5%. Spleen volume (SV) changes were more variable than PDFF and LV reductions and were thus evaluated as a responder analysis (based on percentage of patients with ≥10% reduction or ≥10% increase in SV). Exposure to resmetirom was strongly correlated with LV and SV changes.

LV reduction was correlated with reduction in MRE, MRI-PDFF, TIMP, P3NP, and the SHBG responses to resmetirom (see, e.g., Table 1). Resmetirom reduced LDL-C (20%), triglycerides (21%), ApoB (20%), Lp (a) (30%), independent of cirrhosis stage. BP was reduced by 4-5 mm. Resmetirom was safe and well-tolerated.

TABLE 1

| | Pearson | | Spearman | |
|---|---|---|---|---|
| CFB in: | % CFB LV | CFB LV | CFB LV | p value |
| TIMP | 0.500 | 0.350 | 0.369 | 0.007 |
| P3NP | 0.351 | 0.294 | 0.238 | 0.086 |
| MRI-PDFF (w 16) | 0.331 | 0.438 | 0.371 | 0.006 |
| MRE (w 16) | 0.327 | 0.273 | 0.347 | 0.014 |
| AST (w 52) | 0.197 | 0.254 | 0.191 | 0.170 |
| SHBG | −0.282 | −0.274 | −0.344 | 0.012 |

CFB, change from baseline;
LV, liver volume;
TIMP, tissue inhibitor metalloproteinase;
P3NP, amino terminal procollagen peptide;
w, week.

Resmetirom treatment of patients with NASH cirrhosis for up to 52 weeks was safe and effective at lowering markers of CV risk and NASH fibrosis.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A method of treating well-compensated cirrhotic nonalcoholic steatohepatitis (NASH) comprising administering to a human subject in need thereof a therapeutically effective amount of resmetirom or a pharmaceutically acceptable salt thereof.

2. The method of claim 1, wherein the therapeutically effective amount of resmetirom or the pharmaceutically acceptable salt thereof is 60 mg to 80 mg.

3. The method of claim 1, wherein the therapeutically effective amount of resmetirom or the pharmaceutically acceptable salt thereof is 60 mg.

4. The method of claim 1, wherein the therapeutically effective amount of resmetirom or the pharmaceutically acceptable salt thereof is 80 mg.

5. The method of claim 1, wherein the therapeutically effective amount of resmetirom or the pharmaceutically acceptable salt thereof is 100 mg.

6. A method of reducing liver volume comprising administering to a human subject in need thereof a therapeutically effective amount of resmetirom or a pharmaceutically acceptable salt thereof, wherein the human subject in need thereof has well-compensated cirrhotic nonalcoholic steatohepatitis (NASH).

7. The method of claim 6, wherein the therapeutically effective amount of resmetirom or the pharmaceutically acceptable salt thereof is 60 mg to 80 mg.

8. The method of claim 6, wherein the therapeutically effective amount of resmetirom or the pharmaceutically acceptable salt thereof is 60 mg.

9. The method of claim 6, wherein the therapeutically effective amount of resmetirom or the pharmaceutically acceptable salt thereof is 80 mg.

10. The method of claim 6, wherein the therapeutically effective amount of resmetirom or the pharmaceutically acceptable salt thereof is 100 mg.

* * * * *